(12) United States Patent
Heismann et al.

(10) Patent No.: US 7,139,362 B2
(45) Date of Patent: Nov. 21, 2006

(54) COMPUTER TOMOGRAPH COMPRISING ENERGY DISCRIMINATING DETECTORS

(75) Inventors: Björn Heismann, Erlangen (DE); Thomas von der Haar, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 92 days.

(21) Appl. No.: 10/508,405

(22) PCT Filed: Mar. 13, 2003

(86) PCT No.: PCT/DE03/00818

§ 371 (c)(1),
(2), (4) Date: Sep. 21, 2004

(87) PCT Pub. No.: WO03/079903

PCT Pub. Date: Oct. 2, 2003

(65) Prior Publication Data

US 2005/0105687 A1    May 19, 2005

(30) Foreign Application Priority Data

Mar. 21, 2002 (DE) ................ 102 12 638

(51) Int. Cl.
*A61B 6/03* (2006.01)
*H05G 1/64* (2006.01)
(52) U.S. Cl. ............................ 378/5; 378/19
(58) Field of Classification Search .............. 378/5, 378/19, 98, 98.8; 250/370.09
See application file for complete search history.

(56) References Cited

U.S. PATENT DOCUMENTS 4,537,202 A * 8/1985 Mancini et al. ............ 600/525
4,651,005 A * 3/1987 Baba et al. ............... 250/360.1
6,248,990 B1    6/2001 Pyyhtiä et al.
6,355,923 B1    3/2002 Pyyhtiä et al.

FOREIGN PATENT DOCUMENTS

| DE | 199 04 904 A1 | 8/2000 |
| DE | 697 11 902 T2 | 11/2002 |
| DE | 101 27 267 A1 | 12/2002 |
| EP | 0 782 375 A1 | 7/1997 |
| JP | 2000-189409 | 7/2000 |

OTHER PUBLICATIONS

E. Hell et al., "The evolution of scintillating medical detectors", Nuclear Instruments and Methods in Physics Research Section A, 2000, pp. 40-48.
A. Shor et al.,Spectroscopy with pixelated CdZnTe gamma detectors—experiment versus theory, Nuclear Instruments & Methods in Physics Research Section A, 2000, pp. 47-54.
Schmidt, "MeBelektronik in der Kernphysik", B.G. Teubner Stuttgart 1986, pp. 169-177.

* cited by examiner

*Primary Examiner*—Edward J. Glick
*Assistant Examiner*—Chih-Cheng Glen Kao
(74) *Attorney, Agent, or Firm*—Harness, Dickey & Pierce, P.L.C.

(57) ABSTRACT

The invention relates to a computer tomograph comprising a detector unit (2) consisting of a plurality of detectors (1) for identifying X-ray radiation (40). According to the invention, the individual detectors (1) of the detector unit (2) are configured to receive incident quanta of the X-ray radiation (40) and to record the received X-ray radiation (40), both in terms of its intensity and in terms of the quantum energy of the individual X-ray quanta of the received X-ray radiation (40). The invention also relates to a corresponding method for identifying X-ray radiation by means of a computer tomograph that comprises a detector unit (2) consisting of a plurality of detectors (1).

14 Claims, 3 Drawing Sheets

COMPUTER TOMOGRAPH COMPRISING ENERGY DISCRIMINATING DETECTORS

This application is the national phase under 35 U.S.C. § 371 of PCT International Application No. PCT/DE03/00818 which has an International filing date of Mar. 13, 2003, which designated the United States of America and which claims priority on German Patent Application number DE 102 12 638.0 filed Mar. 21, 2002, the entire contents of which are hereby incorporated herein by reference.

FIELD OF THE INVENTION

The present invention generally relates to a computer tomograph and to a method for verification of X-ray radiation by use of a detector unit which includes a large number of detectors.

BACKGROUND OF THE INVENTION

Examinations are carried out with the aid of computer tomographs in many medical problem situations. Examinations such as these are also carried out for test purposes in a number of machine construction fields, in particular in materials science and flight safety.

X-ray radiation is used in this case because these solid bodies, for example non-metallic bodies, can be partially penetrated, so that it is possible to obtain knowledge about the distribution of materials within the body being analyzed.

The use of X-ray radiation has the disadvantage that, beyond a certain dose, it can damage biological tissue. Therefore, particularly in medicine, it is desirable to keep the radiation dose required for a measurement low.

In order to verify X-ray radiation, it is known that this radiation can be absorbed by specific scintillation materials, with the energy in the absorbed X-ray quanta being converted to light. The number of photons produced per X-ray quantum is in this case generally approximately proportional to their quantum energy.

A photodiode converts the light to a current which is digitized by an analog/digital converter. Since the self-absorption of the light in the scintillation material frequently has molecules added to it, which cause the frequency of the light that is produced to be shifted, in order in this way to prevent self-absorption of the light that is produced.

Furthermore, specific semiconductor materials in which the incident X-ray radiation can produce charge carriers, are also known for verification of X-ray radiation. The number of charge carriers produced per X-ray quantum is in this case generally approximately proportional to their quantum energy.

The known detectors for verification of X-ray radiation make use of the effects described above. In this case, it should be noted that the known integrating detectors produce only one measured value per measurement. The light flashes or charges which are produced by the large number of X-ray quanta received in each measurement period are thus integrated up over the duration of the measurement period. The intensity of the received X-ray radiation (the number of received X-ray quanta of medium quantum energy per unit time) is then obtained by division of the value integrated up by the detector by the medium quantum energy per X-ray quantum, which can be determined stochastically.

Since the measurement X-ray radiation emitted for measurement purposes in computer tomography normally has a polychromatic spectrum, hardening effects must be taken into account in this context. When the measurement X-ray radiation emitted from a radiation source passes through a measurement object, the X-ray radiation is subject in some cases to severe suppression of low-energy components of its spectrum, depending on the materials it is passing through and on the length of the beam path through the materials. The scattered radiation is thus shifted in the same way as the medium quantum energy of the received X-ray quanta toward higher energies in the spectrum.

In order to verify the two-dimensional distribution and thus to create an image of the incident X-ray radiation, it is known for a large number of identical detectors to be combined to form a detector unit for detection of incident radiation, and for emission of corresponding image information. The detectors are in this case preferably arranged alongside one another on a plane, in the form of an array.

This results in a different value for the actual medium quantum energy per X-ray quantum, as a result of hardening effects for each detector in a detector unit as a function of the material distribution in the measurement object being analyzed. This actual value can be determined only approximately by means of stochastic methods. Particularly in areas in which different materials in the measurement object being analyzed are adjacent to one another (for example bone edges), the approximate determination of the medium quantum energy per X-ray quantum is subject to major errors, despite numerical corrections.

A further disturbance variable on the measurement of X-ray radiation by use of computer tomographs is the scattered radiation, which is pronounced to a greater or lesser extent depending on the measurement object being analyzed. The scattered radiation may make up several tens of percentage points of the emitted measurement X-ray radiation, depending on the spectrum of the emitted measurement X-ray radiation and on the nature of the measurement object being analyzed. This leads to a considerable deterioration in the contrast in the measurement result obtained from the detectors in the detector unit.

A scattered radiation grid, through which only X-ray quanta which are in a specific direction and which have a specific energy (and which are thus important for the measurement) can pass, is therefore provided upstream of the detector unit in known computer tomographs. The scattered radiation grid generally has a specific collimator system in the form of a lamella arrangement, so that X-ray quanta of the emitted measurement X-ray radiation which strike the lamella walls are also absorbed.

The provision of a scattered radiation grid accordingly means that a certain percentage of the radiation quanta of measurement X-ray radiation which is emitted for measurement purposes is absorbed in the scattered radiation grid, and can thus no longer be detected by the detectors.

In consequence, the intensity of the radiation emitted for measurement purposes must be increased appropriately, owing to the scattered radiation grid.

In medical applications, this unavoidably leads to an increased patient dose. Furthermore, the scattered radiation can frequently also not be sufficiently well suppressed by the provision of a scattered radiation grid.

SUMMARY OF THE INVENTION

An object of an embodiment of the present invention is to provide a computer tomograph and a method for verification of X-ray radiation by way of a detector unit which includes large number of detectors and in which an adverse effect on the measurement result caused by scattered radiation quanta or hardening effects is easily and reliably avoided.

The object may be achieved by a computer tomograph having:

a radiation source for emission of X-ray radiation with a predetermined intensity and a predetermined spectrum;

a detector unit, which comprises a large number of detectors, for verification of X-ray radiation, with the individual detectors in the detector unit being designed to receive incident X-ray quanta in the X-ray radiation and to detect the number of X-ray quanta in the received X-ray radiation whose quantum energy exceeds a predetermined threshold value;

a transmission device for transmission of the information detected by the detectors in the detector unit to an evaluation device and an evaluation device which is designed to calculate a measurement result from a measurement object through which the X-ray radiation has passed on the basis of the information detected by the detectors in the detector unit, with the individual detectors in the detector unit being designed to detect both the intensity and the quantum energy of the individual detectors equipped to receive impinging X-ray quanta in the received X-ray radiation and, for each measurement period, to emit a spectrum which, in addition to information about the number of X-ray quanta of medium quantum energy received in each measurement period, and hence the intensity, also contains information about the respective quantum energy of the X-ray quanta, and thus the spectrum of the received X-ray radiation; and in that the evaluation device is also designed to calculate the measurement result from the measurement object on the basis of the information detected by the detectors relating to the intensity and quantum energy of the individual X-ray quanta in the received X-ray radiation, taking into account the intensity and the spectrum of the X-ray radiation emitted from the radiation source.

Since the detectors in the detector unit in the computer tomograph according to an embodiment of the present invention are designed to receive incident X-ray radiation and to detect the intensity and the quantum energy of the individual X-ray quanta in the received X-ray radiation, a spectrum is emitted at the output of the detectors in the detector unit, instead of a single measured value per measurement period, which spectrum contains not only information about the number of X-ray quanta of medium quantum energy (intensity) received per measurement period, but also information about the respective quantum energy of the X-ray quanta (the spectrum) in the received X-ray radiation.

A design such as this allows a particularly detailed measurement result to be calculated in a particularly simple and reliable manner from a measurement object being analyzed by comparison of the intensity and of the spectrum of the X-ray radiation emitted from a radiation source with the intensity detected by the detectors in the detector unit for the computer tomograph according to an embodiment of the invention and the spectrum of the received X-ray radiation.

The information obtained in this way can be used to further suppress influences caused by scattered radiation, in addition to a scattered radiation grid which may be provided.

Furthermore, by analysis of the spectrum obtained, it is possible to reliably to detect hardening effects in the received X-ray radiation, such as those which occur at bone edges, on the basis of the shift in the spectrum of the received X-ray radiation. The hardening effects detected in this way can then be taken into account, and possibly corrected, appropriately in the further processing of the information obtained from the detectors in the detector unit.

Furthermore, during the further processing of the information obtained from the detectors in the detector unit, it is advantageous that a quantitative evaluation of the spectral data obtained with the inventive computer tomographs (for example by $\rho$-Z transformation) is possible with the methods known for conventional computer tomographs.

Furthermore, the electronics for the detectors for the computer tomograph according to an embodiment of the invention have considerably less analog parts than the electronics of conventional detectors, since there is no need to integrate up a large number of result elements produced by X-ray quanta in the received X-ray radiation. The electronics for the computer tomograph according to the invention may thus be smaller, cheaper and more resistant to disturbances.

In summary, according to an embodiment of the present invention, it is possible to produce a computer tomograph having a detector unit, which includes a large number of detectors, for verification of X-ray radiation, in which the adverse effect on the measurement result caused by scattered radiation quanta or hardening effects is simply and reliably avoided.

According to a first preferred embodiment, the detectors in the detector unit have a large number of parallel-connected comparators, each having a threshold value, and each comparator has an associated counter, and the comparators are designed to increment the respectively associated counter by one unit when the quantum energy of an X-ray quantum in the received X-ray radiation exceeds the threshold value of the respective comparator.

A detector design such as this makes it possible to detect both the intensity and the spectrum of the received X-ray radiation in a particularly simple manner. Furthermore, since the number of received X-ray quanta with a specific quantum energy are also detected by all the counters in the comparators with lower threshold values, no results are rejected. The number of X-ray quanta with a quantum energy within a threshold value range can then easily be calculated from the difference between the counts of two comparators with adjacent threshold values. In this case, use is made of the correlation of the counting rates of counters, so that the statistical error does not rise during the subtraction process.

The threshold values of the comparators are preferably freely variable, so that the computer tomograph according to an embodiment of the invention can be matched to different measurement objects to be analyzed, and to different measurement methods.

The information obtained from the detectors in the detector unit can be processed further particularly easily by the detectors in the detector unit having a large number of pulse logic devices. The pulse logic devices provide time normalization of the output signals from the comparators. In this case, one pulse logic device is in each case connected downstream from each of the comparators, and is connected upstream of each of the counters.

The detectors in the detector unit preferably have a receiving area for the X-ray radiation, which receiving area is formed from gadoliniumoxysulfide ceramic, bismuth germanium oxide or lutetium oxyorthosilicate. These very fast scintillator materials allow a counting rate, which is preferably used in the computer tomograph according to the invention, of up to 10 MHz for pixel sizes of about $\frac{1}{50}$ mm$^2$.

Alternatively, however, the detectors may also have a direct-conversion receiving area for receiving the X-ray radiation, which receiving area is preferably formed from cadmium zinc telluride or cadmium telluride.

The advantage of direct-conversion detectors is, in particular, that a large proportion of the evaluation electronics which are required for further processing of a signal produced by the detector can be integrated in the detectors, thus making it possible to reduce the complexity of the detector unit, not least as a result of the reduction in the number of lines to be passed out.

An object on which an embodiment of the present invention is based is also achieved by a method for verification of X-ray radiation by way of a computer tomograph which has a detector unit comprising a large number of detectors, having the following steps:

detection of the number of X-ray quanta whose quantum energy exceeds a predetermined threshold value in the X-ray radiation received by means of the individual detectors in the detector unit;

transmission of the information obtained by means of the detectors in the detector unit to an evaluation device and calculation of a measurement result from a measurement object through which the X-ray radiation has passed, by means of the evaluation device on the basis of the information detected by the detectors in the detector unit, with both the intensity and the quantum energy of the individual X-ray quanta in the X-ray radiation received by means of the individual detectors in the detector unit being detected, and, in that, in each measurement period, the individual detectors in the detector unit emit a spectrum which, in addition to information about the number of X-ray quanta of medium quantum energy received in each measurement period, and hence the intensity, also contains information about the respective quantum energy of the X-ray quanta, and thus the spectrum of the received X-ray radiation, and in that the measurement result from the measurement object is calculated by means of the evaluation device on the basis of the information detected by the detectors relating to the intensity and quantum energy of the individual X-ray quanta in the received X-ray radiation, taking into account the intensity and the spectrum of the X-ray radiation emitted from a radiation source.

A method such as this makes it possible to correct for scattered radiation influences and hardening effects in a particularly simple and reliable manner by comparison of the intensity and of the spectrum of the X-ray radiation which is emitted from a radiation source with the intensity, as detected by the detectors in the detector unit, and the spectrum of the received X-ray radiation, and thus to calculate a particularly detailed measurement result from a measurement object being analyzed.

With a design such as this, by comparison of the intensity and of the spectrum of the X-rays emitted from a radiation source with the intensity and spectrum of the X-rays received by the detectors of the detector unit of the computer tomograph according to the invention and the spectrum of the received X-ray radiation, it is possible to calculate a particularly detailed measurement result from a measurement object being analyzed, in a particularly simple and reliable manner.

According to a first embodiment of a method of the invention, the step of detection of the X-ray quanta which are received by way of the detector in the detector unit comprises the following steps:

detection of a signal which is produced in the detector as a consequence of a received X-ray quantum, hose signal level is proportional to the quantum energy in the received X-ray quantum;

comparison of the signal level with a large number of predetermined threshold values;

incrementation of a counter, which is in each case associated with one range between two adjacent threshold values, by one unit when the signal level of the signal is in the range between the two adjacent threshold values.

Since the counts of the counters thus receive both information about the number of X-ray quanta received and about the respective quantum energy of the received X-ray quanta at the end of a measurement period, it is simple to indicate both the intensity and the spectrum of the received X-ray radiation on the basis of the counts of the counters.

According to an alternative, second, particularly preferred embodiment of the method according to the invention, the step of detection of the X-ray quanta which are received by way of the detector in the detector unit comprises the following steps:

detection of a signal which is produced in the detector as a consequence of a received X-ray quantum, whose signal level is proportional to the quantum energy in the received X-ray quantum;

comparison of the signal level with a large number of predetermined threshold values;

incrementation of counters, which are each associated with one threshold value, by one unit when the signal level of the signal exceeds the respective threshold value.

One particularly advantageous feature of this procedure is that no results are rejected since the number of received X-ray quanta with a specific quantum energy are also detected by all the counters with a lower threshold value. The number of X-ray quanta with a quantum energy within a threshold value range can then easily be calculated from the difference between the counts of the counters of two comparators with adjacent threshold values.

It is also advantageous for a signal which is produced in the detector as a consequence of a received X-ray quantum to be rejected if the determined signal level of the signal is lower than a lowest threshold value.

Another particularly advantageous feature of the method according to the invention is for the threshold values to be freely variable.

According to one particularly preferred embodiment, the method according to the invention also comprises the following steps:

transmission of the information obtained by means of the detectors to an evaluation device;

calculation of a measurement result from a measurement object through which the X-ray radiation has passed, by means of the evaluation device on the basis of the information detected by the detectors and taking into account the intensity and the spectrum of the X-ray radiation emitted from a radiation source.

A method such as this makes it possible to correct for scattered radiation influences and hardening effects in a particularly simple and reliable manner by comparison of the intensity and of the spectrum of the X-ray radiation which is emitted from a radiation source with the intensity, as detected by the detectors in the detector unit, and the spectrum of the received X-ray radiation, and thus to calculate a particularly detailed measurement result from a measurement object being analyzed.

BRIEF DESCRIPTION OF THE DRAWINGS

Further advantages, features and details of the invention will become evident from the description of illustrated exemplary embodiments given hereinbelow and the accompanying drawings, which are given by way of illustration only and thus are not limitative of the present invention, wherein identical elements are provided with the same reference symbols and, wherein.

DETAILED DESCRIPTION OF THE PREFERRED EMBODIMENTS

Figure 1:
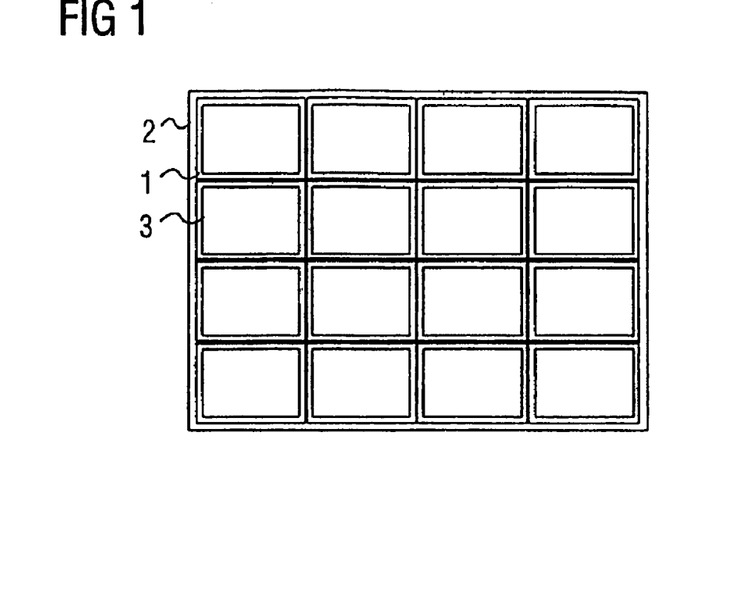
FIG. 1 shows a detector unit, which includes a large number of detectors, for a computer tomograph for verification of X-ray radiation.

FIG. 1 shows a detector unit, which includes a large number of detectors, for a computer tomograph for verification of X-ray radiation.

The individual detectors 1 in the detector unit 2 are each designed to be the same, and each have a receiving area 4 for X-ray radiation.

In the illustrated preferred embodiment, the receiving areas 4 of the detectors have a scintillator material, in which impinging X-ray quanta are converted to light. In this case, the number of photons which are produced by a received X-ray quantum is approximately proportional to the quantum energy of the received X-ray quantum. In FIG. 1, bismuth germanium oxide ($Bi_4Ge_3O_{12}$) is used as the scintillator material. However, alternatively, gadoliniumoxysulfide ($Gd_2O_2S$) ceramic or lutetium oxyorthosilicate ($Lu_2SiO_5$) are also highly suitable owing to the speed of these scintillator materials.

However, alternatively, the receiving areas 3 of the detectors may also be formed from cadmium zinc telluride (CdZnTe) or cadmium telluride (CdTe), since these materials can emit an electrical signal directly in response to a received X-ray quantum (that is to say without having to pass through light). The value/the level of the signal (in the form of a charge, a voltage or a current that is produced) is in this case approximately proportional to the quantum energy in the received X-ray quantum. Direct-conversion detectors have the particular advantage that some of the evaluation electronics which are used for further processing (but which are not shown) for the detectors can be integrated directly in the respective detector.

Figure 2:
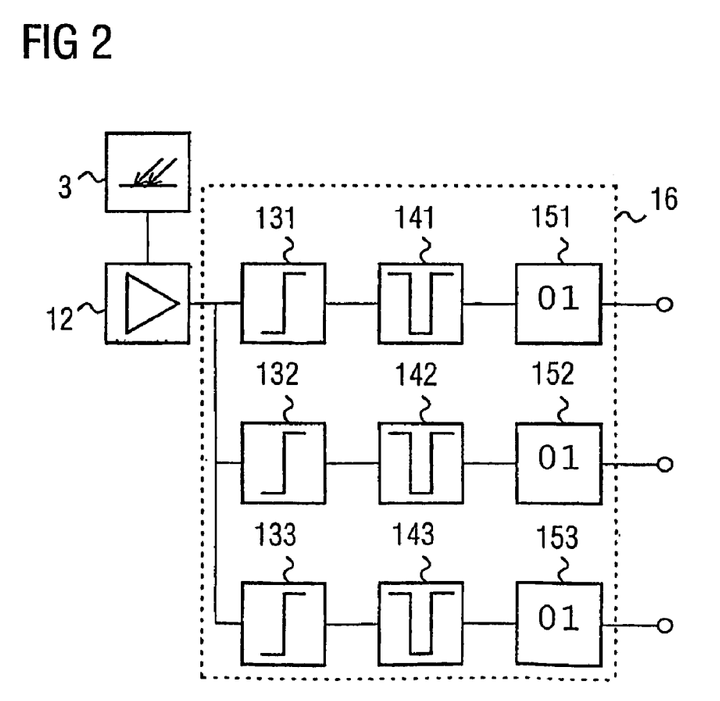
FIG. 2 shows, schematically, major elements of a detector for the computer tomograph according to the invention, based on one particularly preferred embodiment.

FIG. 2 shows, schematically, major elements of a detector for the computer tomograph according to the invention, based on one particularly preferred embodiment.

As explained above, a received X-ray quantum produces a signal in the receiving area 3 of the detector 1 illustrated in FIG. 2, whose signal level is proportional to the quantum energy of the received X-ray quantum. This signal is amplified by an amplifier 12.

A detection circuit 16, which has three parallel-connected comparators 131, 132 and 133, is connected to the amplifier 12. Each of the parallel-connected comparators 131, 132 and 133 is assigned a different freely variable threshold value. In the illustrated example, the comparator 131 is assigned the lowest threshold value, and the comparator 133 is assigned the highest threshold value.

The comparators 131, 132 and 133 are designed in order to compare the signal emitted from the amplifier 12 with their respective threshold value, and to emit a positive signal if the signal received from the amplifier 12 is higher than the respective threshold value.

A pulse logic device 141, 142 and 143 is in each case connected in series with the comparators 131, 132 and 133. Each of the pulse logic devices 141, 142 and 143 is designed to provide time normalization of the output signals from the comparators 131, 132 and 133. A counter 151, 152 and 153 is in each case connected in series with the pulse logic device 141, 142 and 143.

A positive signal emitted from the respective comparator 131, 132 and 133 and normalized by the respective pulse logic device 141, 142 and 143 results in the respective counter 151, 152 and 153 being incremented by one unit.

In this case, the pulse logic devices 141, 142 and 143 are preferably synchronized to one another, and have a common control line, which is not shown.

When, in the particularly preferred embodiment of a detector for the computer tomograph according to an embodiment of the invention as shown in FIG. 2, an X-ray quantum is thus received, whose quantum energy is higher than the threshold value of the comparator 132 and is thus also higher than the threshold value of the comparator 131, but is lower than the threshold value of the comparator 133, then both the comparator 131 and the comparator 132 emit a positive output signal. As a result of this, the counters 151 and 152 are incremented upward by one unit. The comparator 133 on the other hand emits a negative output signal, and the counter 153 associated with the comparator 133 remains unchanged.

When, in the illustrated example, an X-ray quantum is received whose quantum energy is higher than the threshold value of the comparator 131 but is lower than the threshold value of the comparator 132 and is thus also lower than the threshold value of the comparator 133, then, in a corresponding manner, only the counter 151 is incremented by one, while, in contrast, the counters 152 and 153 remain unchanged.

If, in contrast, an X-ray quantum is received whose quantum energy is lower than the threshold value of the comparator 131, then the X-ray quantum is not detected by any of the counters 151, 152 or 153.

It is thus possible by skilful choice of the lowest threshold value to exclude from the start scattered radiation inputs, since they are not detected by any of the counters.

As will be clearly evident from the examples described above, the number of received X-ray quanta whose quantum energy corresponds to a respective threshold value range can easily be calculated by the difference between the counts of the counters in comparators for adjacent threshold values.

The particularly preferred embodiment which is illustrated in FIG. 2 allows, owing to better clarity, only a spectral distinction between X-ray quanta in four quantum energy ranges (lower than the threshold value of the comparator 131, between the threshold values of the comparators 131 and 132, between the threshold values of the comparators 132 and 133, and higher than the threshold value of the comparator 133).

Figure 3:
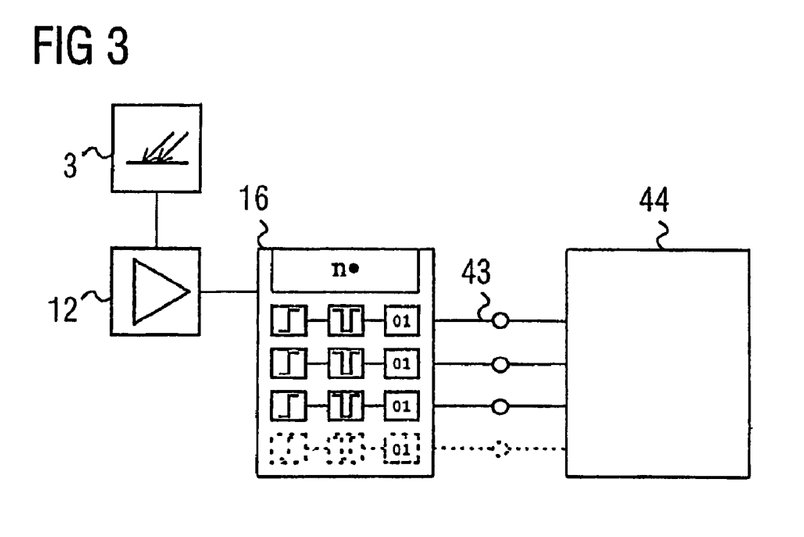
FIG. 3 shows the principle of a development of the detector shown in FIG. 2.

In order on this basis to achieve a higher spectral resolution for the received X-ray radiation, as is desirable in practice, all that is necessary is to provide in the detection circuit 16, a higher number of parallel switched comparators with different threshold values. As indicated in FIG. 3, a pulse logic device and a counter can once again be associated with each comparator. In consequence, a virtually indefinitely fine spectral resolution of the X-ray radiation received by the receiving area 3 of the detector 1 can thus be achieved in a simple manner.

The detector 1, as described above, in the detector unit 2 for the computer tomograph according to an embodiment of the invention thus detects both the intensity and the quantum energy of the individual X-ray quanta in the received X-ray radiation.

Figure 4:
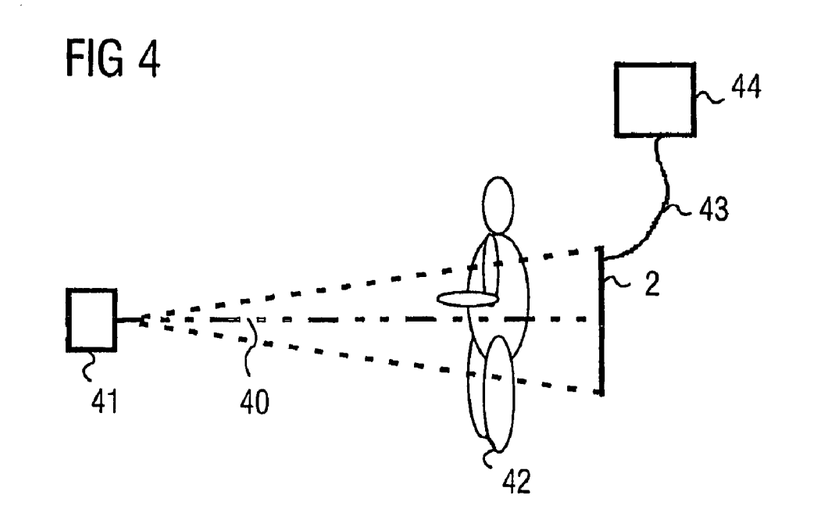
FIG. 4 shows, schematically, major elements of one preferred measurement layout with the computer tomograph according to an embodiment of the invention.

According to one particularly preferred embodiment, which is illustrated in FIG. 4, it is also particularly advantageous for the computer tomograph according to an embodiment of the invention to have, in addition to a radiation source 41 for emission of X-ray radiation 40 with a predetermined intensity and a predetermined spectrum, a transmission device 43 for transmission of the information detected by the detectors 1 in the detector unit 2 to an evaluation device 44.

In this case, the evaluation device 44 is preferably designed to use the information detected by the detectors 1 in the detector unit 2 to calculate a measurement result from a measurement object 42 through which the X-ray radiation 40 from the radiation source 41 has passed, taking into account the intensity and the spectrum of the X-ray radiation 40 emitted from the radiation source 41.

This design makes it possible to obtain a particularly accurate and error-free measurement result, since scattered radiation influences as well as hardening effects can be effectively detected, quantified, and thus also corrected.

In the following text, with reference to FIG. 5 and using a flow chart, a preferred embodiment of the method according to an embodiment of the invention is described, for verification of X-ray radiation by way of a computer tomograph which has a detector unit 2 including a large number of detectors 1.

According to an embodiment of the invention, in the case of the method, both the intensity and the quantum energy of a single X-ray quantum in the received X-ray radiation 40 received by way of one detector 1 in the detector device 2 are detected.

Figure 5:
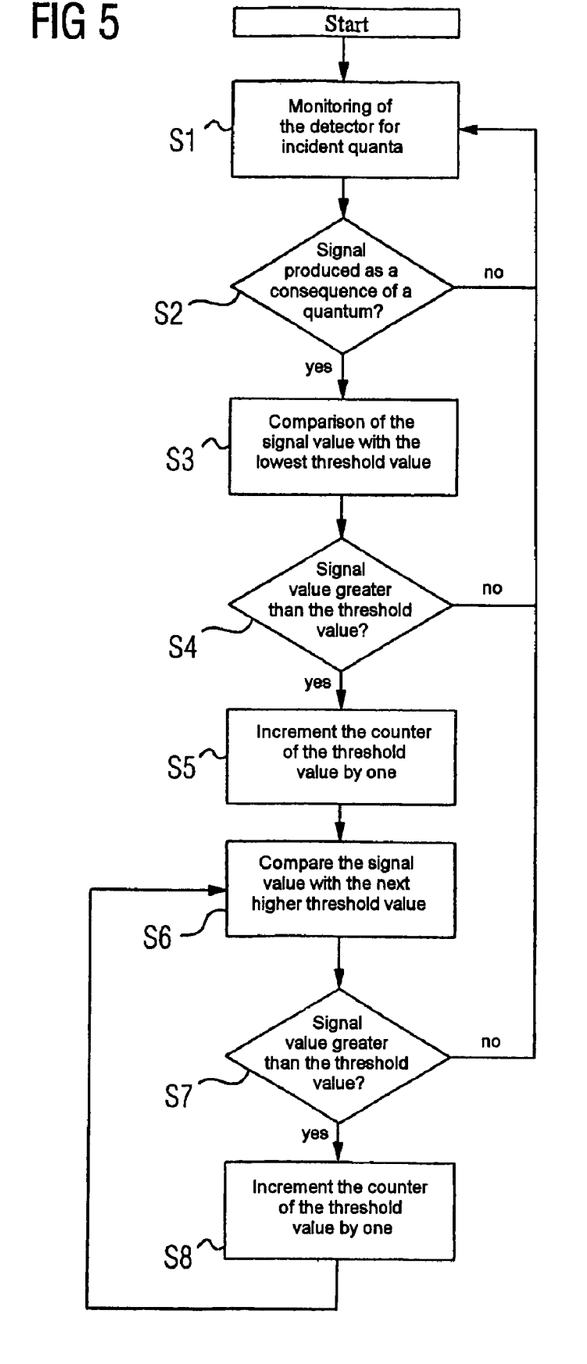
FIG. 5 shows a flowchart of one particularly preferred embodiment of the method according to the invention for verification of X-ray radiation, by means of a computer tomograph which has a detector unit comprising a large number of detectors.

According to the preferred embodiment illustrated in FIG. 5, the step of detection of the X-ray quanta received by way of a respective detector 1 in the detector unit 2 has the following steps:

In a first step S1, the detector 1 is continuously monitored for incident X-ray quanta, in order to detect an analog signal emitted from the detector 1 as a consequence of an X-ray quantum having been received. In this case, the detector 1 is designed such that the value (the level) of the emitted signal is proportional to the quantum energy of the received X-ray quantum (as is the case, by way of example, with scintillation detectors). This emitted signal may, for example, be an electric current, a voltage or a charge with a specific magnitude.

In step S2, if a signal which is produced as a consequence of an X-ray quantum being received by the detector 1 is detected, then the value of the signal that is produced is first of all compared with a first, lowest threshold value in order to determine the quantum energy of the received X-ray quantum, causing the signal, in step S3.

If a decision is made in step S4 that the value of the signal is higher than the lowest threshold value, then a counter 151 which is associated with the lowest threshold value is incremented by one unit in the next step S5.

Otherwise, the method returns to step S1, in which the detector 1 carries out continuous monitoring for incident X-ray quanta.

If the decision as made in the step S4 that the value of the signal is higher than the lowest threshold value, then the signal, then, after incrementing the counter 151 (see step S5) that is associated with the lowest threshold value, the signal is compared with the next-higher threshold value, in step S6.

If the decision is made in the following step S7 that the value of the signal is higher than this next-higher threshold value, then the counter 152, 153 which is associated with this threshold value is also incremented in the step S8.

The signal is then once again compared with the respective next-higher threshold value in step S6.

If the decision is made in step S7 that the signal value is lower than the respective threshold value, then the method returns to step S1, in which the detector 1 carries out continuous monitoring for incident X-ray quanta.

It should be noted that individual steps in the method described in conjunction with FIG. 5 (in particular the steps S3, S4, S5 and S6, S7, S8), if they are carried out by the electronic detection circuit as shown in FIG. 2, are preferably not processed in serial form, as shown in FIG. 5, but in parallel form. In this case, clocking of the steps in FIG. 2 is predetermined by the pulse logic device, and is preferably several MHz.

As is obvious from the embodiment according to the invention, explained with reference to FIG. 5, that a signal generated by the detector 1, as a consequence of a received X-ray quantum is rejected if the signal value is lower than the lowest threshold value. It is thus possible to largely exclude scattered radiation influences by a suitable choice of the lowest threshold value.

However, in principle, the threshold values are in this case freely variable, so that it is even feasible to use a lowest threshold value of zero, or close to zero. A low threshold value such as this has the advantage that no event is rejected.

Once the method described above has been carried out, the number of incident X-ray quanta with a quantum energy which corresponds to a specific threshold range can easily be determined by the difference between the counts of the counters which are associated with adjacent threshold values.

In the described particularly preferred embodiment, the method illustrated in FIG. 5 is carried out in a detection circuit 16 which is integrated in each detector 1 in the detector unit 2 for the computer tomograph according to an embodiment of the invention.

According to one alternative embodiment of the method according to the invention, which is not specifically illustrated, it is also possible, in contrast to the embodiment described above, to in each case increment by one unit only that counter which is in each case associated with a range between two adjacent threshold values, while, in contrast, the other counters remain constant. This allows the number of incident X-ray quanta with a quantum energy associated with a specific threshold range to be emitted directly without any further calculations. This alternative embodiment of the method according to the invention can be implemented in circuitry particularly easily in that an AND gate with inverting input is connected upstream. In this case, the outputs of the comparators for adjacent threshold values can be connected (possibly via a pulse logic device) to the inputs of this AND gate.

In the method according to an embodiment of the invention, it is also particularly advantageous for the method also to have the steps of transmission of the information obtained by way of the detectors 1 to an evaluation device 44, and calculation of a measurement result from a measurement object 42 through which the X-ray radiation 40 has passed by way of the evaluation device 44. In this case, the measurement result is calculated by the evaluation device 44 on the basis of the information detected by the detectors 1, taking into account the intensity and the spectrum of the X-ray radiation 40 emitted from a radiation source 41. During the calculation of the measurement result for the measurement object 42, it is thus possible to correct not only for the scattered radiation influences but also for hardening influences, with a high degree of error confidence.

In summary, according to an embodiment of the present invention, the detection of both the intensity and the spectrum of X-ray radiation 40 which is received by way of a detector 1 in a detector unit 2 for a computer tomograph allows a computer tomograph and a method to be provided for verification of X-ray radiation 40 by way of a detector unit 2 which includes a large number of detectors 1, in which any adverse effect on the measurement result caused by scattered radiation quanta or hardening effects can easily and reliably be avoided.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A computer tomograph, comprising:
a radiation source for emission of X-ray radiation with a predetermined intensity and a predetermined spectrum;
a detector unit, including a plurality of detectors, for verification of X-ray radiation, wherein individual detectors of the detector unit are designed to receive incident X-ray quanta in the X-ray radiation and to detect the number of X-ray quanta in the received X-ray radiation whose quantum energy exceeds a predetermined threshold value;
a transmission device for transmission of the information detected by the detectors in the detector unit; and
an evaluation device, designed to calculate a measurement result from a measurement object through which the X-ray radiation has passed on the basis of the information detected by the detectors in the detector unit, wherein the individual detectors in the detector unit are designed to detect both the intensity and the quantum energy of the individual X-ray quanta in the received X-ray radiation, and, for each measurement period, to emit a spectrum which, in addition to information about the number of X-ray quanta of medium quantum energy received in each measurement period, and hence the intensity, also contains information about the respective quantum energy in the X-ray quanta, and thus the spectrum of the received X-ray radiation; wherein the evaluation device is also designed to calculate the measurement result from the measurement object on the basis of the information detected by the detectors relating to the intensity and quantum energy of the individual X-ray quanta in the received X-ray radiation, taking into account the intensity and the spectrum of the X-ray radiation emitted from the radiation source; wherein the detectors in the detector unit include a plurality of parallel-connected comparators, each having a threshold value and each including an associated counter, the comparators being designed to increment the respectively associated counter by one unit when the quantum energy of an X-ray quantum in the received X-ray radiation exceeds the threshold value of the respective comparator; and wherein the detectors in the detector unit include a plurality of pulse logic devices, one pulse logic device being connected downstream from the respective comparators and upstream of the respective counters, the pulse logic devices providing time normalization of the output signals from the comparators.

2. The computer tomograph as claimed in claim 1, wherein the threshold values of the comparators are freely variable.

3. The computer tomograph as claimed in claim 1, wherein the detectors in the detector unit include a receiving area for the X-ray radiation, the receiving area being formed from at least one of gadoliniumoxysulfide ceramic, bismuth germanium oxide and lutetium oxyorthosilicate.

4. The computer tomograph as claimed in claim 1, wherein the detectors in the detector unit include a direct-conversion receiving area for the X-ray radiation, the receiving area being formed from at least one of cadmium zinc telluride and cadmium telluride.

5. A method for verification of X-ray radiation by way of a computer tomograph which has a detector unit including a plurality of detectors, the method comprising:
detecting a number of X-ray quanta whose quantum energy exceeds a predetermined threshold value of the X-ray radiation received, using the individual detectors in the detector unit;
transmitting the information detected; and
calculating a measurement result from a measurement object through which the X-ray radiation has passed, on the basis of the information detected by the detectors, wherein both the intensity and the quantum energy of the individual X-ray quanta in the X-ray radiation received by the individual detectors in the detector unit are detected, wherein the individual detectors in the detector unit emit, for each measurement period, a spectrum which, in addition to information about the number of X-ray quanta of medium quantum energy received in each measurement period, and hence the intensity, also contains information about the respective quantum energy of the X-ray quanta, and thus the spectrum of the received X-ray radiation, wherein the measurement result from the measurement object is calculated on the basis of the information detected by the detectors relating to the intensity and quantum energy of the individual X-ray quanta in the received X-ray radiation, taking into account the intensity and the spectrum of the X-ray radiation emitted from a radiation source, and wherein the detectors in the detector unit include a plurality of parallel-connected comparators, each having a threshold value and each including an associated counter, the comparators being designed to increment the respectively associated counter by one unit when the quantum energy of an X-ray quantum in the received X-ray radiation exceeds the threshold value of the respective comparator, and wherein the detectors in the detector unit include a plurality of pulse logic devices, one pulse logic device being connected downstream from the respective comparators and upstream of the respective counters, the pulse logic devices providing time normalization of the output signals from the comparators.

6. The method for verification of radiation as claimed in claim 5, wherein the detection of the X-ray quanta which are received by way of the detector in the detector unit comprises:

detecting a signal, produced in the detector, as a consequence of a received X-ray quantum, whose signal level is proportional to the quantum energy in the received X-ray quantum;

comparing the signal level with a large number of predetermined threshold values; and incrementing a counter, which is in each case associated with one range between two adjacent threshold values, by one unit when the signal level of the signal is in the range between the two adjacent threshold values.

7. The method for verification of radiation as claimed in claim 6, wherein a signal, which is produced in the detector as a consequence of a received X-ray quantum, is rejected if the determined signal level of the signal is lower than a lowest threshold value.

8. The method for verification of radiation as claimed in claim 7, wherein the threshold values are freely variable.

9. The method for verification of radiation as claimed in claim 6, wherein the threshold values are freely variable.

10. The method for verification of radiation as claimed in claim 5, wherein the detection of the X-ray quanta which are received by use of the detector in the detector unit comprises:

detecting a signal which is produced in the detector as a consequence of a received X-ray quantum, whose signal level is proportional to the quantum energy in the received X-ray quantum;

comparing the signal level with a large number of predetermined threshold values; and incrementing counters, which are each associated with one threshold value, by one unit when the signal level of the signal exceeds the respective threshold value.

11. The method for verification of radiation as claimed in claim 10, wherein a signal, which is produced in the detector as a consequence of a received X-ray quantum, is rejected if the determined signal level of the signal is lower than a lowest threshold value.

12. The method for verification of radiation as claimed in claim 11, wherein the threshold values are freely variable.

13. The method for verification of radiation as claimed in claim 10, wherein the threshold values are freely variable.

14. An apparatus for verification of X-ray radiation using a computer tomograph, comprising:

means, including a plurality of individual detectors, for detecting a number of X-ray quanta whose quantum energy exceeds a predetermined threshold value of the X-ray radiation received;

means for transmitting the information detected; and means for calculating a measurement result from a measurement object through which the X-ray radiation has passed, on the basis of the information detected, wherein both the intensity and the quantum energy of the individual X-ray quanta in the X-ray radiation received by the individual detectors are detected, wherein the individual detectors emit, for each measurement period, a spectrum which, in addition to information about the number of X-ray quanta of medium quantum energy received in each measurement period, and hence the intensity, also contains information about the respective quantum energy of the X-ray quanta, and thus the spectrum of the received X-ray radiation, wherein the measurement result from the measurement object is calculated on the basis of the information detected by the detectors relating to the intensity and quantum energy of the individual X-ray quanta in the received X-ray radiation, taking into account the intensity and the spectrum of the X-ray radiation emitted from a radiation source, wherein the detectors include a plurality of parallel-connected comparators, each having a threshold value and each including an associated counter, the comparators being designed to increment the respectively associated counter by one unit when the quantum energy of an X-ray quantum in the received X-ray radiation exceeds the threshold value of the respective comparator, and wherein the detectors include a plurality of pulse logic devices, one pulse logic device being connected downstream from the respective comparators and upstream of the respective counters, the pulse logic devices providing time normalization of the output signals from the comparators.

* * * * *